Figure 1:
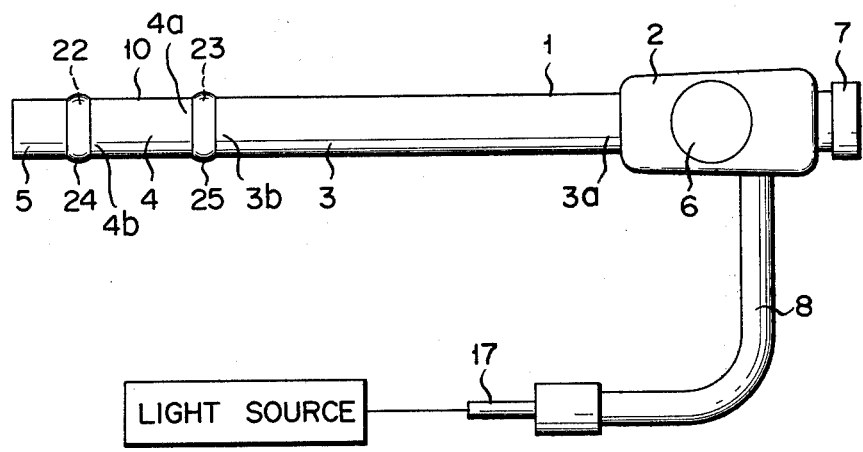

United States Patent [19]

Hosono

[11] 4,347,837
[45] Sep. 7, 1982

[54] STRUCTURE FOR PREVENTING THE BREAKAGE OF END PORTIONS OF A PROTECTIVE COVERING FOR THE ADJUSTABLE BEND SECTION OF AN ENDOSCOPE

[75] Inventor: Saburo Hosono, Hachioji, Japan
[73] Assignee: Olympus Optical Co., Ltd., Tokyo, Japan
[21] Appl. No.: 187,543
[22] Filed: Sep. 16, 1980
[30] Foreign Application Priority Data
  Sep. 17, 1979 [JP] Japan .................. 54-128388
[51] Int. Cl.³ ............................. A61B 1/06
[52] U.S. Cl. ................................. 128/6
[58] Field of Search .................. 128/772, 4-12, 128/103

[56] References Cited

U.S. PATENT DOCUMENTS

| 3,162,214 | 12/1964 | Bazinet, Jr. ............ | 138/120 |
| 3,256,875 | 6/1966 | Tsepelev et al. ........ | 128/6 |
| 3,583,393 | 6/1971 | Takahashi ............... | 138/103 |
| 3,670,721 | 6/1972 | Fukami et al. .......... | 128/6 |
| 3,788,304 | 1/1974 | Takahashi ............... | 128/6 |

FOREIGN PATENT DOCUMENTS

| 143130 | 1/1950 | Fed. Rep. of Germany ......... | 128/6 |
| 235270 | 1/1951 | Fed. Rep. of Germany ......... | 128/6 |
| 1014709 | 8/1957 | Fed. Rep. of Germany ......... | 128/6 |
| 2850021 | 11/1978 | Fed. Rep. of Germany ......... | 128/6 |

Primary Examiner—Robert Peshock

[57] ABSTRACT

A structure for preventing the breakage of both end portions of a protective covering for an adjustable bend section of an endoscope consists of annular elastic members retaining elasticity and adhesivity even at high temperature. Each of the elastic members of the structure comprises a first section which is fixed by thread to the respective end portions of a protective covering which is made of elastic material and surrounds a core assembly, and the respective end portions of which are fastened to the respective end portions of the core assembly by the thread; and a second section which is made of the same material as that of the first section and extends from the first section toward the intermediate part of the protective covering to be fixed to the respective end portion of the protective covering. With the above-mentioned structure, the annular elastic members are not deteriorated even at high temperature. If, therefore, the protective covering loses elasticity upon exposure to high temperature, a stress resulting from the flexing of the adjustable bend section of the endoscope is uniformly adsorbed by the whole length of the second portion of the annular elastic member. Consequently, a stress is not concentrated at particular regions of both end portions of the protective covering. As a result, both end portions of the protective covering are resistant to cracking or any other form of damage, thereby prolonging the effective life of the protective covering.

5 Claims, 2 Drawing Figures

STRUCTURE FOR PREVENTING THE BREAKAGE OF END PORTIONS OF A PROTECTIVE COVERING FOR THE ADJUSTABLE BEND SECTION OF AN ENDOSCOPE

This invention relates to a structure for preventing the breakage of both thread-fastened end portions of protective covering for an adjustable bend section of an endoscope.

Hitherto, an adjustable bend section constituting part of that section of an endoscope which is inserted into a coeliac caving of, for example, a human body is enclosed in a tubular protective covering made of electric material such as rubber. Both end portions of the protective covering are tightly fastened by threads to seal the adjustable bend section of the endoscope in a fluid-tight state. An adhesive agent which neither expands nor shrinks after solidification is applied to the threads and both end portions of the protective covering fastened by the threads, thereby fixing the threads to the thread-fastened end portions of the protective covering.

When subjected to an external force, the thread-fastened end portion of a protective covering for such conventional endoscopes neither expands nor shrinks in the axial direction of the adjustable bend section of the endoscope. At a temperature approximating atmospheric temperature, the intermediate portion of the protective covering which is between both end portions and is not fastened by threads still has an elastic property. Where, therefore, the adjustable bend section of the endoscope is flexed, most of the resultant stress is absorbed in the elastic intermediate portion of the protective covering. Consequently, since a great concentrated stress does not act on a boundary region between the intermediate portion and both end portions of the protective covering, little there is tending for the occurrence of cracks in the boundary region.

However, conventional industrial endoscopes applied in observing the interior of an apparatus (such as an aircraft engine whose run is stopped for examination and which must be warmed up in a short time) and whose interior reaches as high a temperature as 150° C., or conventional medical endoscopes subjected to a sterilizing process at a high temperature of, for example, 135° C. have the drawbacks that when exposed to the above-mentioned high temperatures, the protective covering of the industrial or medical endoscope is deteriorated with loss of elasticity. The conventional adhesive agents applied to the thread-fastened portions originally lack elasticity. When, therefore, the adjustable bend section of the endoscope is flexed, a great concentrated stress is applied to a boundary region between the intermediate portion and both thread-fastened end portions of the protective covering, readily giving rise to the appearance of cracks in the boundary region and rendering the protective covering as a whole nondurable.

The object of this invention is to provide a simple structure for preventing the breakage of both threadfastened end portions of a protective covering for the adjustable bend section of an endoscope.

A structure embodying this invention for attaining the above-mentioned object, comprises an elastic member made of resin retaining elasticity and adhesivity both at normal temperature and at high temperature and comprising a first section which encloses the adjustable bend section of an endoscope and surrounds both end portions of an elongate protective convering, and is wound with fixing threads; and a second section which extends from the first section toward the intermediate part of the adjustable bend section of the endoscope and is fixed to the protective covering.

When the above-mentioned structure is applied to an endoscope, a stress resulting from the flexing of the adjustable bend section of an endoscope is less concentrated at a boundary between the thread-fastened portion of each end of the protective covering and that intermediate portion of the adjustable bend section which is not wound with threads. Where, therefore, the protective covering is subjected to a deteriorating environment, as by exposure to high temperature, a crack or any other form of damage does not arise at the boundary. Consequently, the structure embodying this invention is well adapted for use with an industrial endoscope designed to observe the interior of mechanical equipment which is kept at high temperature or a medical endoscope which has to be sterilized at high temperature.

Figure 2:
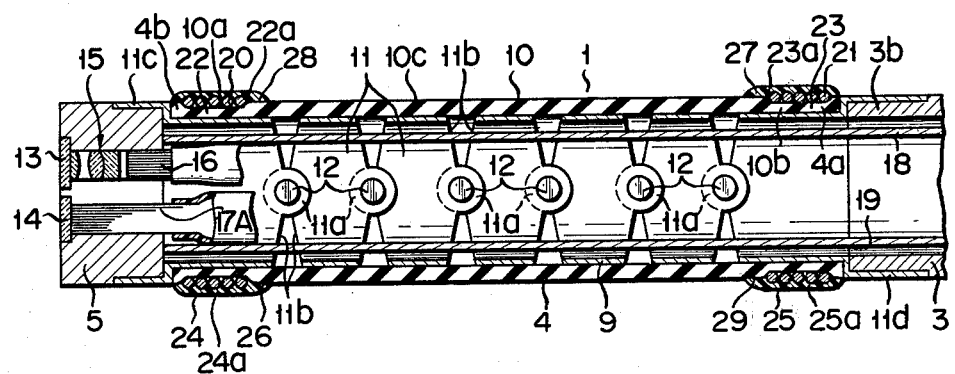

This invention will be fully understood from the following detailed description with reference to the accompanying drawings in which:

FIG. 1 is a front view of an endoscope having a structure embodying this invention; and FIG. 2 is a longitudinal cross sectional view of the distal end section and the adjustable bend section of an endoscope of FIG. 1, particularly showing the longitudinal cross sectional view of the thread-fastened end portions of the protective covering.

Referring to FIG. 1, an endoscope in which both end portions of a protective covering for the adjustable bend section of the endoscope are provided with a structure embodying this invention for saving said end portions from damage comprises an elongated insertion section 1 and an control section 2, from the distal end of which the insertion section 1 extends. The insertion section 1 comprises an elongated flexible sheath 3 whose proximal end 3a is fixed to the control section 2; an elongated adjustable bend section 4 whose proximal end 4a is connected to the distal end 3b of the elongated flexible sheath 3; and a distal end section 5 whose proximal end is connected to the distal end 4b of the adjustable bend section 4. The proximal end of the control section 2 is provided with an ocular section or eye piece 7. A light guide cable 8 extends from one lateral side of the control section 2. An illumination optical fiber bundle 17 which conducts light issued from a light source extends through the light guide cable 8. Another lateral side of the control section 2 disposed substantially at right angles to the aforesaid one lateral side of the control section 2 is fitted with a knob 6 for adjusting the extent to which the adjustable bend section 4 of the endscope is to be flexed as desired.

Referring to FIG. 2, the adjustable bend section 4 of the endoscope comprises an elongated core ring assembly 9 and a hollow cylindrical covering 10 which is made of elastic material such as rubber and encloses the core ring assembly 9. The core ring assembly 9 comprises series-arranged core rings 11 whose end planes 11b are each inclined toward the intermediate part of the core rings 11 from the lugs 11a axially extending from the diametrically opposite points on the peripheral wall of the respective core rings 11. The lugs 11a of adjacent core rings 11 are rotatably supported by pins 12. Therefore, the relative rotation of the core ring 11 enables the adjustable bend section 4 of the endoscope to be freely flexed. The distal end portion of the outermost core ring 11 of the core ring assembly 9 is not provided with either lug 11a inclined end plane 11b. Instead, the distal end portion of the outermost core ring 11 is formed into a large diameter flange 11c, thereby securely supporting the proximal end of the distal end section 5 of the endoscope. An observation window 13 and illumination window 14 are formed in the tip end face of the distal end section 5. An observation lens system 15 aligned with the observation window 13 is received in the distal end section 5. One end of an image guide (observation optical fiber bundle) 16 is located in the position in which an observed image is focused by the observation lens system 15, and the other end of the image guide 16 is optically connected to the eyepiece 7.

A light guide (illumination optical fiber bundle) 17A also extends through the insertion section 1 of the endoscope. One end of the light guide 17A is optically connected to the illumination window 14. The other end of the illumination light guide 17A is optically connected to the light guide 17 set in the light guide cable 8.

The tip of the rearmost core ring 11 at the proximal end of the core assembly 9 is not provided with either lug 11a or inclined end plane 11b. Instead, the tip is formed into a large diameter flange 11d, thereby securely supporting the distal end 3b of the sheath 3.

Control wires 18, 19 extend through the adjustable bend section 4 and sheath 3 of the endoscope. These wires 18, 19 are fixed at one end to the rear side of the distal end section 5 of the endoscope, and at the other end to a mechanism (not shown) cooperating with the knob 6 mounted on the control section 2 of the endoscope to actuate the adjustable bend section 4. The rotation of the knob 6 causes the adjustable bend section 4 to be flexed in a desired direction with a prescribed curvature radius by means of the wires 18, 19. Illumination and observation by an endoscope provided with a structure embodying this invention are carried out in the same manner as the conventional type, description thereof being omitted.

Description is now given with reference to FIG. 2 of a structure embodying the present invention. Both end portions 10a, 10b of the protective covering 10 are respectively wound with threads 20, 21 such as silk yarn having high heat resistivity, thereby fixing both end portions 10a, 10b to the distal and proximal end portions of the core assembly 9 respectively. Those of both end portions 10a, 10b of the protective covering 10 which are tightened by the threads 20, 21 respectively are referred to as "the thread-fastened portions 22, 23." Both end portions 10a, 10b of the protective covering are fully enclosed in rolls of threads 20, 21 respectively. An adhesive which retains elasticity and adhesivity even when exposed to a high temperature ranging from 150° to 200° C. is applied in the form of a layer to the surface of both end portions 10a, 10b and the threads 20, 21 to be spread beyond the thread-fastened portions 22, 23 toward the intermediate part 10c of the protective covering 10, thereby providing annular members or annular layers 24, 25 of adhesive for preventing the breakage of the end portions of the protective covering 10. A structure formed of an adhesive constituting said breakage-preventing member 24, 25 may be prepared from silicone resin or fluoroplastic material.

The breakage-preventing members 24, 25 comprises first portions 24a, 25a for fixing the threads 20, 21 to the thread-fastened portions 22, 23, thereby preventing the threads 20, 21 from being frayed; and second extended portions 26, 27 which are spread from the first section toward the intermediate part 10c of the protective covering 10 and adhered to those portions 28, 29 of the thread-fastened portions 22, 23 of the protective covering 10 which lie adjacent to the intermediate part 10c. In other words, both end portions 10a, 10b of the protective covering 10 respectively comprise an assembly of the thread fastened portions 22 and adjacent portion 28 and an assembly of the thread-fastened portion 23 and adjacent portion 29.

With an industrial endoscope exposed to the aforesaid high temperature or medical endoscope sterilized at such as high temperature as 135° C., the protective covering 10 is more thermally deteriorated until it loses elasticity, as high temperature application or sterilizatllion is repeated. If the thread-fastened portions 22, 23 of the protective covering 10 are coated with a conventional hard adhesive agent and if the protective covering 10 is subject to expansion or shrinkage due to the forceful flexing of the adjustable bend section 4, a stress caused by the flexing is concentrated at boundaries 22a, 23a between the thread-fastened portions 22, 23 and adjacent portions 28, 29, resulting in the occurrence of cracks or form of other form of damage at the boundaries.

If, however, the protective covering 10 is provided with adhesive layers 24, 25 which do not lose elasticity and adhesivity even when repeatedly exposed to the afore-mentioned high temperature, a stress resulting from the expansion or shrinkage of the protective covering 10 caused by the flexing of the adjustable bend section 4 of the endoscope is uniformly absorbed by the whole length of the second portions 26, 27 of the adhesive layers 24, 25. Therefore, a stress is not concentrated at the boundaries 22a, 23a, and there is little tendency to form a crack or any other form of damage at the boundaries, and consequently the effective life of the protective covering 10 is prolonged. The second extended portions 26, 27 are preferred to have a length equivalent to 5 to 30% of the diameter of the adjustable bend section of the endoscope.

What is claimed is:

1. In an endoscope including a control section and an elongated insertion section extending from the control section extending from the control section and comprising an elongated flexible sheath having two ends, one of which is fixed to the control section, a distal end section, and an adjustable bend section comprising an elongated bendable core assembly having two ends, one of which is connected to the other end of the sheath, and the other of which is connected to distal end section, a protective covering which is made of elastic material, has two end portions and an intermediate portion between the two end portions, and encloses substantially the whole length of the core assembly, and threads wound around both end portions of the protective covering to fix both end portions to the core assembly in a sealed state, the improvement wherein the endoscope is further provided with a structure which comprises a first section for overlying and fixing the threads to the end portions of the protective covering, and a second section extending from the first section toward and overlying a portion of the intermediate part of the protective covering and fixed to the end portions of the protective covering, said structure being made of elastic material retaining elasticity and adhesivity at normal and temperatures up to about 200° C., thereby preventing the breakage of the end portions of the protective covering when said covering is subjected to repeated stress.

2. An endoscope according to claim 1, wherein said improvement is a structure comprising an annular member surrounding both end portions of the protective covering.

3. The structure according to claim 2, wherein the adhesive is silicone resin.

4. The structure according to claim 2, wherein the adhesive is fluoroplastic material.

5. The structure according to claim 1, wherein the second section of the structure has a length equivalent to 5 to 30% of the diameter of the adjustable bend position of the endoscope.

* * * * *